(12) United States Patent
Harper

(10) Patent No.: US 9,044,285 B2
(45) Date of Patent: *Jun. 2, 2015

(54) COMPOUND HINGED ROD BENDER

(71) Applicant: Globus Medical, Inc., Audubon, PA (US)

(72) Inventor: Michael Harper, Pottstown, PA (US)

(73) Assignee: Globus Medical Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/293,691

(22) Filed: Jun. 2, 2014

(65) Prior Publication Data

US 2014/0260484 A1 Sep. 18, 2014

Related U.S. Application Data

(63) Continuation of application No. 13/219,295, filed on Aug. 26, 2011, now Pat. No. 8,770,006.

(60) Provisional application No. 61/377,343, filed on Aug. 26, 2010.

(51) Int. Cl.
*A61B 17/88* (2006.01)
*B21D 7/06* (2006.01)
*B21D 7/024* (2006.01)

(52) U.S. Cl.
CPC ............ *A61B 17/8863* (2013.01); *B21D 7/063* (2013.01); *B21D 7/024* (2013.01)

(58) Field of Classification Search
CPC .. A61B 17/8863; H01R 43/042; B21D 7/024; B21D 7/063
USPC ................. 72/409.01, 409.1, 409.11, 409.19, 72/409.16, 458; 81/349, 350, 351, 383.5, 81/416
See application file for complete search history.

(56) References Cited

U.S. PATENT DOCUMENTS

| 3,704,620 | A | * | 12/1972 | Allen | 72/409.01 |
| 3,747,648 | A | * | 7/1973 | Bauer | 72/409.01 |
| 4,474,046 | A | * | 10/1984 | Cook | 72/409.16 |
| 5,490,409 | A | * | 2/1996 | Weber | 72/409.1 |
| 5,536,270 | A | * | 7/1996 | Songer et al. | 81/420 |
| 5,819,580 | A | * | 10/1998 | Gauthier | 72/409.1 |
| 6,006,581 | A | * | 12/1999 | Holmes | 72/409.1 |
| 6,325,432 | B1 | * | 12/2001 | Sensat | 294/16 |

* cited by examiner

*Primary Examiner* — Teresa M Ekiert

(57) ABSTRACT

A compound rod bender includes a first distal arm, a second distal arm, a rotating and translating barrel, and a compound hinge. The barrel includes a plurality of bending surfaces configured to be selectively positioned to contour a rod. The barrel is positioned on a pivot point between the first and second distal arms. The compound hinge includes at least one additional pivot point configured to increase a bending force when the rod is contoured.

19 Claims, 4 Drawing Sheets

COMPOUND HINGED ROD BENDER

CROSS-REFERENCE TO RELATED APPLICATIONS

This patent application is a Continuation of U.S. patent application Ser. No. 13/219,295 filed on Aug. 26, 2011, now allowed, which claims priority to U.S. Provisional Application No. 61/377,343 filed on Aug. 26, 2010. The content and subject matter of these applications are hereby incorporated by reference in their entirety, including all text and figures, for all purposes.

FIELD OF THE INVENTION

The present disclosure generally relates to a device for bending elongated spinal rods and plates.

BACKGROUND

Bones and bony structures are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses. Typically, weaknesses in the spine are corrected by using devises that fuse one or more vertebrae together. Devices such as rods and plates are utilized to stabilize adjacent vertebrae. However, these rods and plates need to be bent or modified to accommodate the anatomy. Therefore, there is a need for a device which allows a surgeon to easily and accurately bend spinal rods and plates prior to insertion in to the body.

SUMMARY OF THE INVENTION

The present invention discloses a compound rod bender having a first handle arm and a second handle arm coupled to each other at a first pivot point. A body portion is coupled to the first handle arm at a second pivot point and the second handle arm is coupled to a third pivot point. The body portion includes a first and a second distal arm that are configured with first and second rolling elements which are coupled to the distal ends of the first and second distal arms. There is also provided a barrel positioned on a center portion of the body portion. A spinal rod is positionable between the first and second rolling elements and the barrel for bending when the first and second handle arms are actuated.

BRIEF DESCRIPTION OF THE DRAWINGS

The accompanying drawings, which are included to provide a further understanding of the disclosure, are incorporated in and constitute a part of this specification, illustrate aspects of the disclosure and together with the detailed description serve to explain the principles of the disclosure. No attempt is made to show structural details of the disclosure in more detail than may be necessary for a fundamental understanding of the disclosure and the various ways in which it may be practiced.

DETAILED DESCRIPTION OF THE INVENTION

While it is apparent that the invention disclosed herein is well calculated to fulfill the objects stated above, it will be appreciated that numerous modifications and embodiments may be devised by those skilled in the art.

Figure 1:
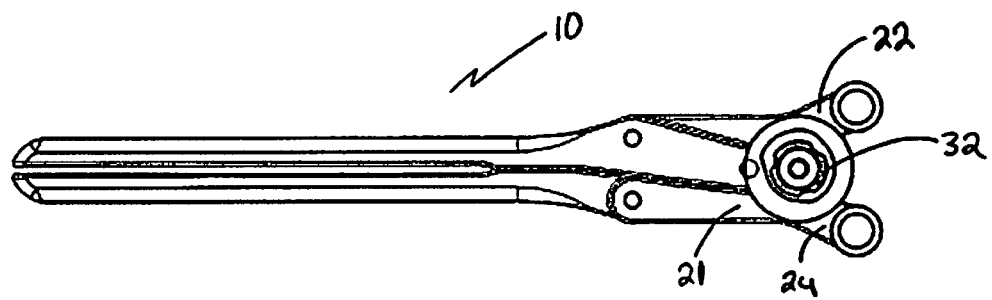
FIG. 1 is a compound rod bender according to the present invention in a closed position.
Figure 2:
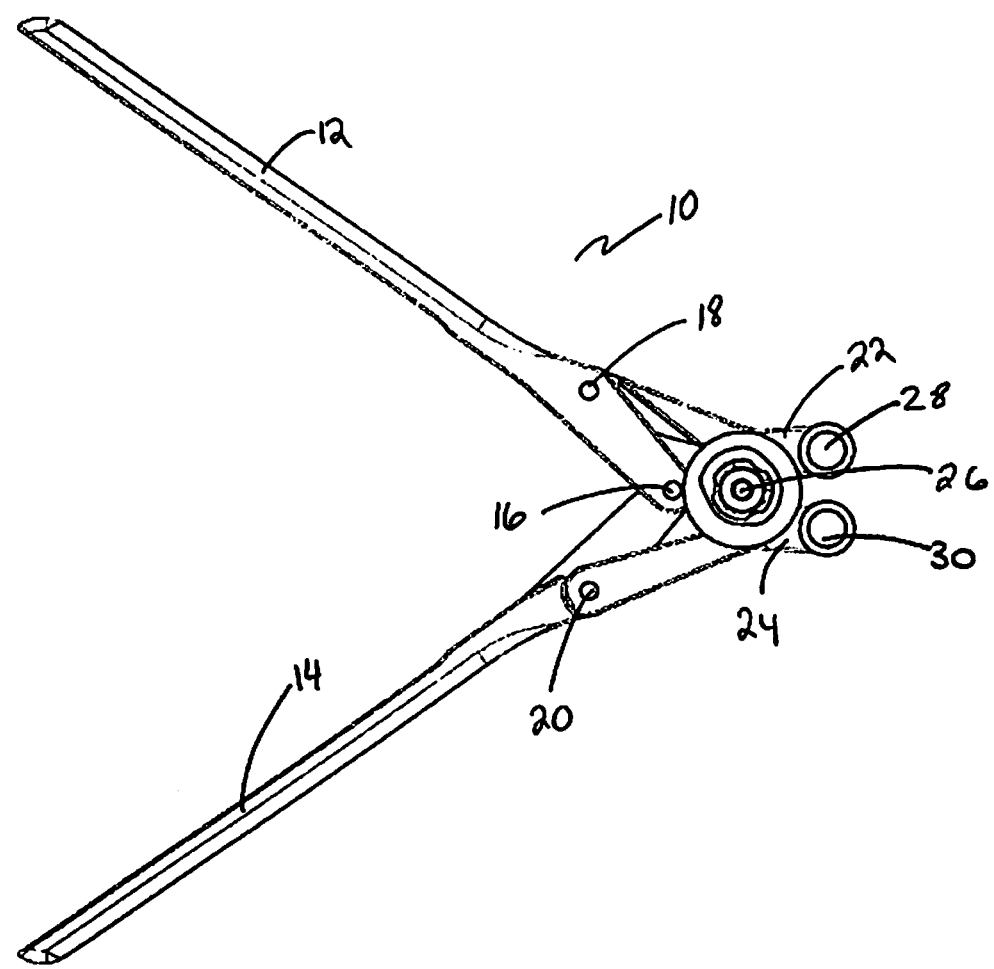
FIG. 2 is a compound rod bender according to the present invention in an open position.
Figure 3:
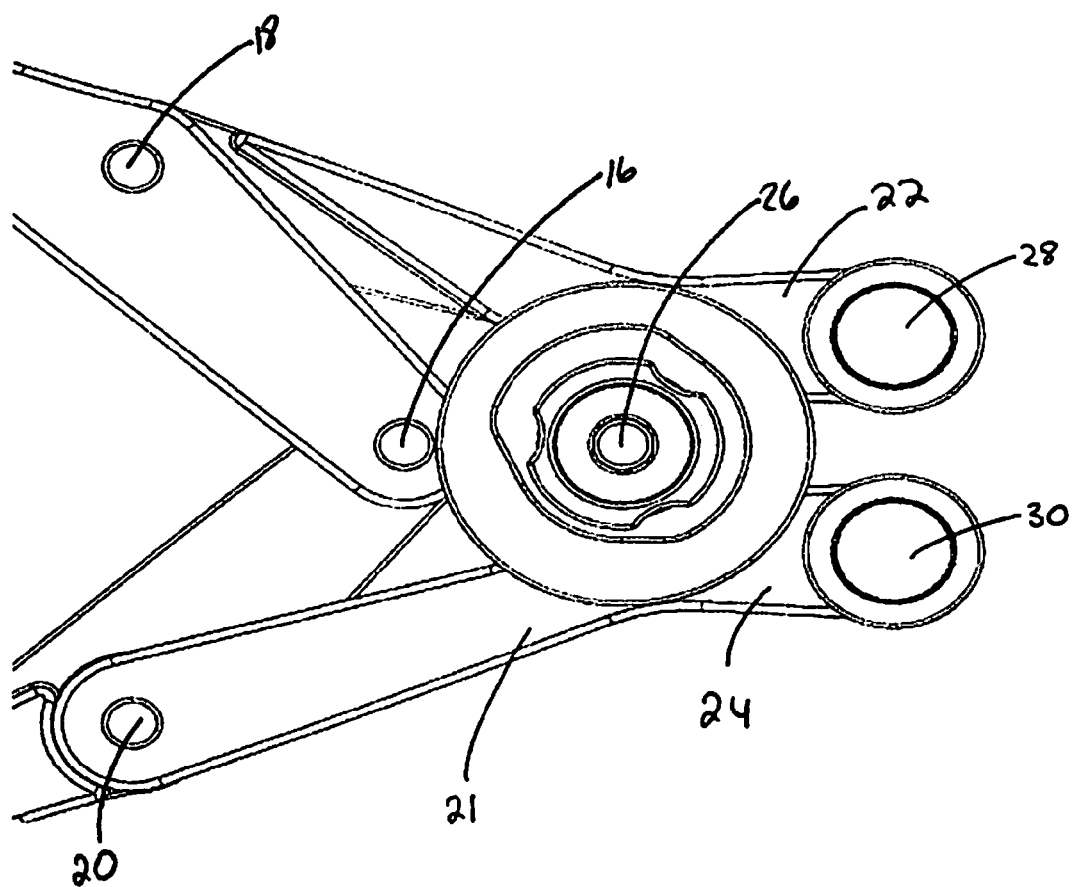
FIG. 3 is a top view of the body portion of the compound rod bender according to the present invention.
Figure 4:
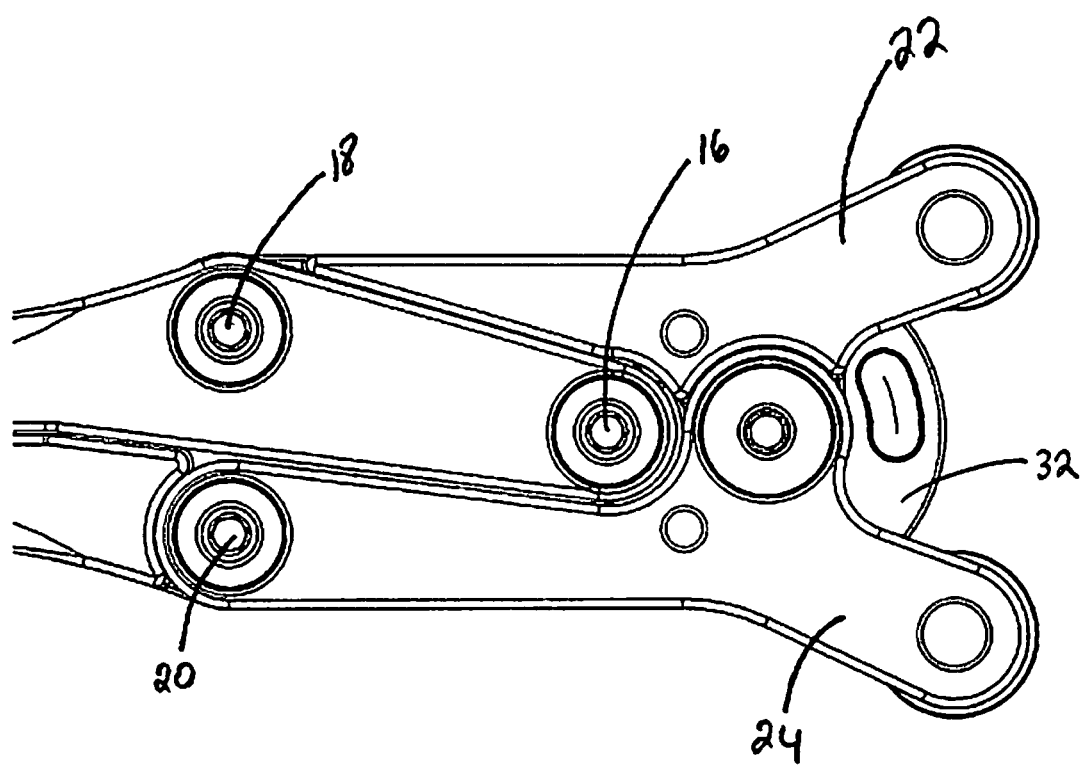
FIG. 4 is a bottom view of the body portion of the compound rod bender in a closed position according to the present invention.
Figure 5:
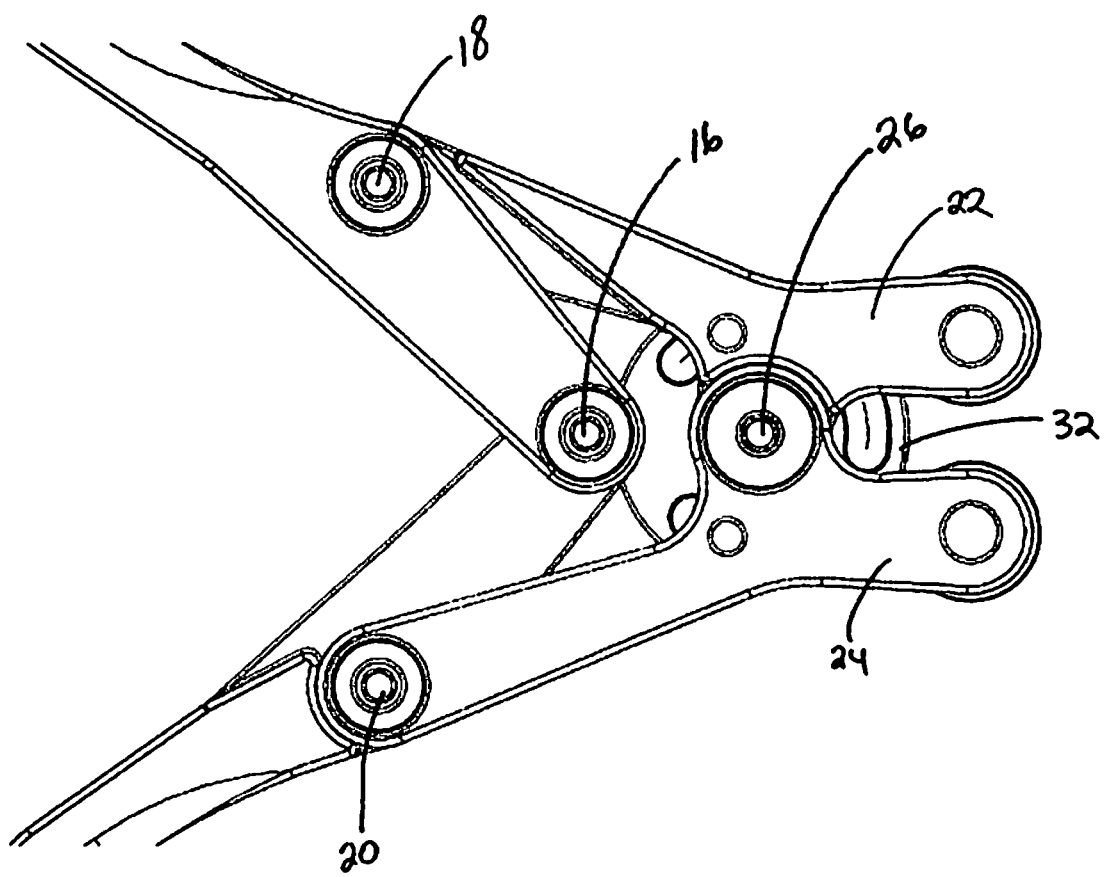
FIG. 5 is a bottom view of the compound rod bender in an open position according to the present invention.

FIGS. 1 and 2 illustrate a compound rod bender 10 in a closed position and in an open position. FIGS. 3-5 illustrate a top view and the bottom view of the rod bender in greater detail. Turning to FIGS. 1-5, the rod bender 10 comprises a first handle arm 12 and a second handle arm 14 that are coupled at a pivot point 16 and pivot points 18 and 20. The first handle arm 12 and the second handle arm 14 are connected to the body 21 of the compound rod bender 10 at pivot points 18 and 20, respectively. The rod bender 10 also comprises a first distal arm 22 and a second distal arm 24 which are configured about pivot point 26. The body 21 of the rod bender 10 is further provided with a first rolling element 28 and a second rolling element 30. The first rolling element 28 is positioned on the distal end of the first distal arm 22 and is configured to be rotatable. The second rolling element 30 is positioned on the distal end of the second distal arm 24 and is configured to be rotatable. The body 21 further provides a rotatable barrel 32 positioned below the first and second rolling elements 28 and 30. The rolling elements 28 and 30 are configured with rotating outer bearing portions which are substantially circular which are coupled to the first and second distal arms by a pin.

The barrel 32 is provided to support a rod when the rod is positioned between the rolling elements and the distal end of the barrel 32. The barrel 32 which is positioned on the pivot point 26 acts as a hinge between the two distal arms 22 and 24. The base portion of the barrel 32 includes a plurality of bending surfaces. Each bending surface can be selectively positioned into the desired operating position. The variety of bending surface contours enables the rod bender to accommodate different size rods, as well as provides for varying severities or contours of bend to the rod. The barrel 32 can be selectively rotated to cause the desired bending surface to be in appropriate position. During the operation of the rod bender 10, when the first and second handle arms 12 and 14 are actuated, a rod that is positioned in the rod bender is bent to accommodate the surgeon's preference. The radius of the bend in the rod can be manipulated by turning the barrel to various positions, as the circumference of the barrel is configured with different radii.

The rod bender of the present invention is operated as follows: First, the desired bending surface on the barrel is rotated and engaged into the operating position. The selected surface of the barrel faces toward the distal end of the instrument and operator positions a spinal rod between the rolling elements and the barrel after the handle arms of the instrument are moderately separated. This causes the distal arms to rotate in an arc upward and inward providing vertical clearance between the two distal arms and the barrel. After clearance is obtained, a suitable rod is then placed onto the selected bending surface of the barrel and the under the first and second rolling elements. A slight grip by the hands of the user will bring the distal arms and the rolling elements down and against the rod trapping it against the bending surface of the barrel. Additional force will bend the rod around the bending surface of the barrel. If a more or less severe bend is desired, the barrel can be rotated so that difference bending surface can be used.

The present invention includes the use of a compound hinge to increase the instruments mechanical advantage. The introduction of three additional pivot points and two lever arms will increase the instrument's output force dramatically, reducing the force required to contour a surgical rod when compared to a traditional rod bender. The relationship between the two sets of lever arms is directly related to the instrument's output force. It uses a compound joint to increase the bending force.

The various features and embodiments of the invention described herein may be used interchangeably with other feature and embodiments. Finally, while it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments which come within the spirit and scope of the present invention.

What is claimed is:

1. A compound rod bender suitable for contouring a rod comprising:
   a first distal arm having a first rolling element positioned on a distal end of the first distal arm;
   a second distal arm having a second rolling element positioned on a distal end of the second distal arm;
   a rotating and translating barrel including a plurality of bending surfaces configured to be selectively positioned to contour the rod, wherein the barrel is positioned on a pivot point between the first and second distal arms; and
   a compound hinge including at least one additional pivot point configured to increase a bending force when the rod is contoured.

2. The compound rod bender of claim 1, wherein the plurality of bending surfaces are each provided with different radii around a circumference of the barrel.

3. The compound rod bender of claim 1, wherein the plurality of bending surfaces are configured to accommodate a variety of different sized rods.

4. The compound rod bender of claim 1, wherein the plurality of bending surfaces are configured to provide for varying severities of bend for the rod.

5. The compound rod bender of claim 1, wherein the rod bender has an open position configured to receive the rod and a closed position configured to bend the rod when the rod is positioned between the first and second rolling elements and the barrel.

6. The compound rod bender of claim 1, wherein the first and second rolling elements are rotatable.

7. The compound rod bender of claim 1, wherein the first and second rolling elements include rotating outer bearing portions.

8. The compound rod bender of claim 1, wherein the barrel may be translated into different positions for accommodating varying rod diameters.

9. The compound rod bender of claim 1 further comprising a first arm and a second arm, wherein the at least one additional pivot point includes a first pivot point coupling the first arm and the second arm, a second pivot point on the first arm, and a third pivot point on the second arm.

10. A spinal rod bending system comprising:
    an elongated spinal rod; and
    a compound rod bender suitable for contouring a rod comprising:
    a first distal arm having a first rolling element positioned on a distal end of the first distal arm;
    a second distal arm having a second rolling element positioned on a distal end of the second distal arm;
    a rotating and translating barrel including a plurality of bending surfaces configured to be selectively positioned to contour the rod, wherein the barrel is positioned on a pivot point between the first and second distal arms; and
    a compound hinge including at least one additional pivot point configured to increase a bending force when the rod is contoured.

11. The system of claim 10, wherein the plurality of bending surfaces are each provided with different radii around a circumference of the barrel configured to accommodate a variety of different sized rods and to provide for varying severities of bend for the rod.

12. The system of claim 10, wherein the rod bender has an open position configured to receive the rod and a closed position configured to bend the rod when the rod is positioned between the first and second rolling elements and the barrel.

13. The system of claim 10, wherein the first and second rolling elements are rotatable and include rotating outer bearing portions.

14. The system of claim 10, wherein the barrel may be translated into different positions for accommodating varying rod diameters.

15. The system of claim 10 further comprising a first arm and a second arm, wherein the at least one additional pivot point includes a first pivot point coupling the first arm and the second arm, a second pivot point on the first arm, and a third pivot point on the second arm.

16. A method of manipulating a spinal rod comprising:
    rotating the barrel of the compound rod bender of claim 1 to select one of the plurality of bending surfaces;
    positioning the spinal rod between the first and second rolling elements and the barrel; and
    applying a force to the compound rod bender such that the spinal rod bends around the barrel.

17. The method of claim 16, wherein before positioning the spinal rod between the first and second rolling elements and the barrel, further comprising pivoting the compound hinge such that the compound rod bender is in an open position configured to receive the spinal rod.

18. The method of claim 16, wherein before positioning the spinal rod between the first and second rolling elements and the barrel, opening the compound rod bender such that the first and second distal arms rotate in an arc upward and inward providing vertical clearance between the first and second distal arms and the barrel.

19. The method of claim 16, wherein the barrel is further rotated to reveal a different one of the plurality of bending surfaces.

* * * * *